US 6,635,059 B2

(12) United States Patent
Randall et al.

(10) Patent No.: US 6,635,059 B2
(45) Date of Patent: Oct. 21, 2003

(54) CANNULATED LOCKING SCREW SYSTEM ESPECIALLY FOR TRANSILIAC IMPLANT

(76) Inventors: Bernard L. Randall, 18360 Ash Creek, Macomb, MI (US) 48044; Berton R. Moed, 25325 Sherwood Dr., Huntington Woods, MI (US) 48070

( * ) Notice: Subject to any disclaimer, the term of this patent is extended or adjusted under 35 U.S.C. 154(b) by 24 days.

(21) Appl. No.: 09/904,392

(22) Filed: Jul. 12, 2001

(65) Prior Publication Data

US 2002/0087161 A1 Jul. 4, 2002

Related U.S. Application Data

(60) Provisional application No. 60/259,656, filed on Jan. 3, 2001.

(51) Int. Cl.$^7$ ............................................... A61B 17/56
(52) U.S. Cl. ....................................................... 606/73
(58) Field of Search ............................. 606/72, 73, 104

(56) References Cited

U.S. PATENT DOCUMENTS

| | | | |
|---|---|---|---|
| 3,683,989 A | | 8/1972 | Follstaedt et al. |
| 3,741,266 A | | 6/1973 | Frailly |
| 4,013,071 A | | 3/1977 | Rosenberg |
| 4,646,752 A | * | 3/1987 | Swann et al. ............... 128/748 |
| 4,773,402 A | | 9/1988 | Asher et al. |
| 4,907,924 A | | 3/1990 | Hellon |
| 5,025,774 A | * | 6/1991 | Martin ......................... 124/89 |
| 5,054,497 A | * | 10/1991 | Kapp et al. .................. 128/748 |
| 5,064,417 A | * | 11/1991 | Andreussi .................... 604/175 |
| 5,129,901 A | | 7/1992 | Decoste |
| 5,395,371 A | * | 3/1995 | Miller et al. ................... 606/61 |
| 5,529,075 A | * | 6/1996 | Clark ........................... 128/898 |
| 5,688,275 A | * | 11/1997 | Koros et al. .................. 606/61 |
| 5,899,902 A | * | 5/1999 | Brown et al. .................. 606/61 |
| 6,048,343 A | | 4/2000 | Mathis et al. |
| 6,354,504 B1 | * | 3/2002 | Sabourault ............. 235/462.42 |
| 2002/0091391 A1 | * | 7/2002 | Cole et al. .................... 606/72 |

OTHER PUBLICATIONS

International Search Report, PCT/US02/00033, Sep. 25, 2002.

(List continued on next page.)

Primary Examiner—Eduardo C. Robert
(74) Attorney, Agent, or Firm—Christopher John Rudy

(57) ABSTRACT

Screw system is useful for transiliac fixation of a sacrum and/or sacroiliac joint and/or for application in other skeletal areas, and includes a cannulated bone screw preferably capable of spanning iliac crests of a patient, having an elongate, hollow body with openings on a first end of the body and on an opposing, second end of the body; a tip on the first end of the body, which preferably is a thread-cutting tip that can engage and thread the ilia or other bone of the patient; a head about the second end of the body, which can be engaged with a surgical tool; and threads on at least part of the body between the first and second ends; a locknut with threads for interference fitting corresponding generally to those of the screw for threading on the screw; and preferably also a washer. Major-minor, pitch-diameter, locking interference fitting can be provided. Associated kit includes at least one such screw system; a guidewire, which is essentially as long as or longer than the elongate hollow body of the screw of the at least one screw system, and over which the screw can pass by the openings in the hollow body of the screw, and which beneficially is rigid and has a drill bit tip; and preferably, a cannulated starter drill and/or a tool set to engage the head of the screw for twisting the screw so that it can thread through bone and/or engage the nut so that it can be tightened onto the first end of the screw.

27 Claims, 2 Drawing Sheets

OTHER PUBLICATIONS

Randall & Moed, U. S. provisional patent application No. 60/259,656 filed Jan. 03, 2001.

Richards Mfg. Co., Memphis, Tenn., Product Release, "Osteoporotic Bone Bolt with Nut–washer Combination," Jan. 26, 1972.

Synthes, Association for the Study of Internal Fixation, "Sacral Bar Kit, Technique Guide," Aug. 1984.

Zimmer, Inc., Warsaw, Ind., "Threaded Bolts and Fixation Sets," Catalog REV 1. p. A38, Feb. 1973.

McKechnie et al. (Eds.), Webster's New Universal Unabridged Dictionary, Second Edition, Dorset & Baber, New York, 1983, pp. 1062, 1661 and 2063.

Horton (Ed.), Machinery's Handbook, Fifteenth Edition, The Industrial Press, New York, 1956, pp. 939, 953–956, 972–977 and 1018–1019.

* cited by examiner

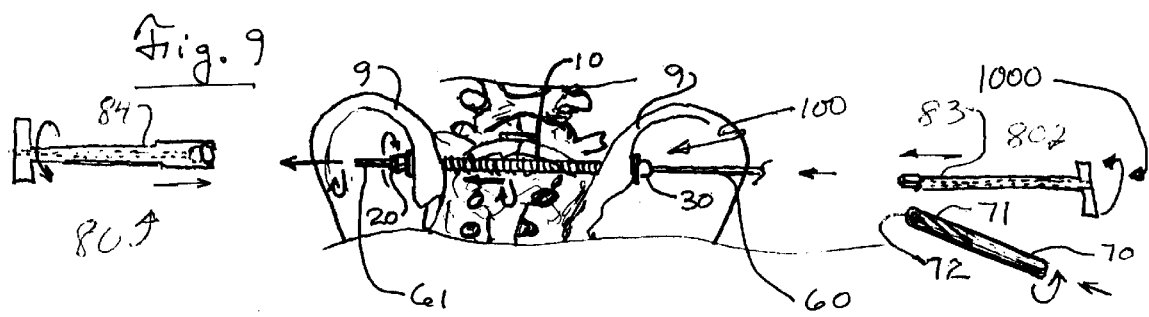
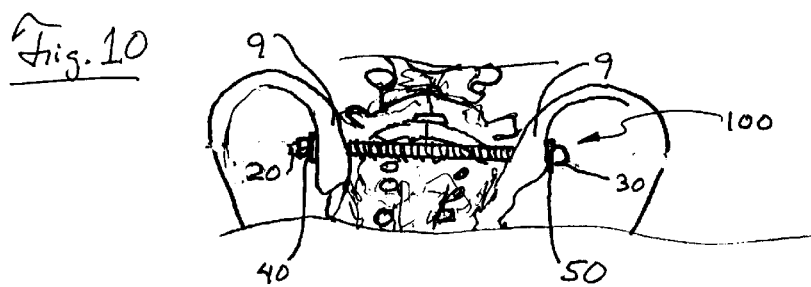
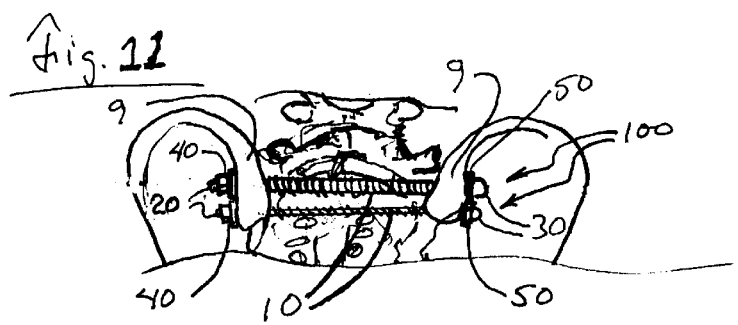

CANNULATED LOCKING SCREW SYSTEM ESPECIALLY FOR TRANSILIAC IMPLANT

CROSS-REFERENCE CLAIM OF PRIORITY

This claims benefit under 35 USC 119(e) of U.S. provisional patent application No. 60/259,656 filed on Jan. 3, 2001 A.D. The invention disclosure of that application is incorporated herein by reference.

FIELD AND PURVIEW OF THE INVENTION

In general, the present invention concerns orthopedic implant systems for fixation of sacral area fractures and application in other skeletal areas. Most particularly, it concerns a system for fixation of the sacrum and/or sacroiliac joints, which can be applied ilium-to-ilium across the sacrum, and which employs a cannulated, locking screw that can be positioned in conjunction with tools including a guidewire through a minimally invasive, percutaneous surgical approach requiring only small incisions.

BACKGROUND TO THE INVENTION

Various bone screws and other fasteners are well known in specific arts within the broad, general field of orthopedics, and use of such devices is widely accepted throughout the orthopedic community as a safe and effective treatment for patients having fractured bones. See, e.g., U.S. Pat. Nos. 4,013,071 which discloses fasteners particularly useful as orthopedic screws; 4,773,402 which discloses a dorsal transacral surgical implant; 5,129,901 which discloses a cannulated orthopedic screw; and 6,048,343 which discloses a bone screw system; plus Richards Manufacturing Co., Osteoporotic Bone Bolt with Nut-washer Combination, Jan. 26, 1972 product release; Zimmer, Inc., Threaded Bolts and Fixation Sets, February 1973 catalog REV-1, page A38; and Synthes catalog, Sacral Bar Kit, August 1984.

Cannulated bone screws, as such, have been produced for a number of years and made available in a variety of sizes to accommodate normal variations in patient anatomies. Compare, the '343 patent to Mathis et al. The use of cannulated screws for hip fractures of the femur is also documented. Note, the '901 patent to Decoste.

Further, the placement of screws in various aspects of the spine for immobilization, and supplemental fixation when performing spinal fusion procedures, has also become widely accepted over the last two decades. Compare, the '402 patent to Asher et al.

Finally, the use of bolts having standard type machine screw threads, to which are mated washers and corresponding nuts, is known in various orthopedic applications. Compare, the Synthes Sacral Bar Kit. It is noted in particular, however useful it may be, that a technique of the type such as that which employs the Synthes kit is highly invasive, requiring large incisions, excision of significant portions of tissue, and employment of massive and unwieldy tools. Such significant and possibly not well tolerated intervention must be weighed seriously when a physician faces possible application of the same to an already traumatized patient who, perhaps among further damage, presents a fractured sacrum in need of fixation through emergency surgery.

It would be desirable to improve upon the foregoing. In particular, it would be desirable to provide for less invasive yet secure fixations of fractured sacra and/or sacroiliac joints through fixation with a fastener spanning iliac crests, notably in traumatized patients. Others have attempted yet failed to fulfill such desiderata.

SUMMARY OF THE INVENTION

The present invention provides, in one aspect, a screw system useful for transiliac fixation of a sacrum and/or a sacroiliac joint and/or for application in other skeletal areas, comprising:

a cannulated bone screw capable of spanning iliac crests of a patient, having an elongate, hollow body with openings on a first end of the body and on an opposing, second end of the body; a tip on the first end of the body, which, optionally but preferably, is a thread-cutting tip, which can engage and thread the ilia of the patient; a head about the second end of the body, which can be engaged with a surgical tool; and threads on at least part of the body between the first and second ends;

a locknut with threads for interference fitting corresponding generally to those of the screw for threading on the screw; and optionally but preferably, a washer.

In other aspects, provided are the locknut itself; and a kit useful for transiliac fixation of a sacrum and/or a sacroiliac joint and/or for application in other skeletal areas, comprising:

at least one aforementioned screw system;

a guidewire, which is essentially as long as or longer than the elongate hollow body of the screw of the at least one screw system, and over which the screw can pass by the openings in the hollow body of the screw, and which, optionally but preferably, is rigid and has a drill bit tip; and optionally but preferably, a cannulated starter drill and/or a tool set to engage the head of the screw for twisting the screw so that it can thread through bone and/or engage the nut so that it can be tightened onto the first end of the screw.

The invention is useful for repair of fractured sacra and fracture dislocations of the sacroiliac joint and/or in application(s) to other skeletal area(s).

Significantly, by the invention, problems in the art are ameliorated if not overcome. In particular, for example, the invention can be employed to repair a fractured sacrum through fixation of the sacrum with the screw spanning the iliac crests, and, what is most important, merely two, small percutaneous incisions are all that are normally required to implant the screw in the patient, who may be otherwise highly traumatized from the injury to his sacrum, if not elsewhere in his body. Accordingly, the invention is highly beneficial for the traumatized patient. Also, the cannulated, self-tapping screw with its locking nut is believed to be a first in the art, particularly with respect to sacral fixation. Beneficially, the system has metal-to-metal, major-minor, pitch-diamter locking interference fit fixation between the screw and locknut. This provides secure percutaneous fixation without significant risk for loosening.

Numerous further advantages attend the invention.

DRAWINGS IN BRIEF

The drawings form part of the specification hereof. With respect to the drawings, which are not necessarily drawn to scale, the following is briefly noted:

FIG. 9 is a rear view of the screw system which is depicted in FIGS. 1–8 being implanted in a human pelvic girdle so as to stabilize the sacrum, with the assistance of a cannulated starter drill, a guidewire, and a set of two cannulated tools.

FIG. 10 is a rear view of the screw system of FIGS. 1–8 in place in the pelvic girdle and stabilizing the sacrum.

FIG. 11 is a rear view of the screw system of FIGS. 1–8, in tandem, in place in the pelvic girdle and stabilizing the sacrum.

DETAIL ADDITIONALLY ILLUSTRATIVE OF THE INVENTION

Figure 1:
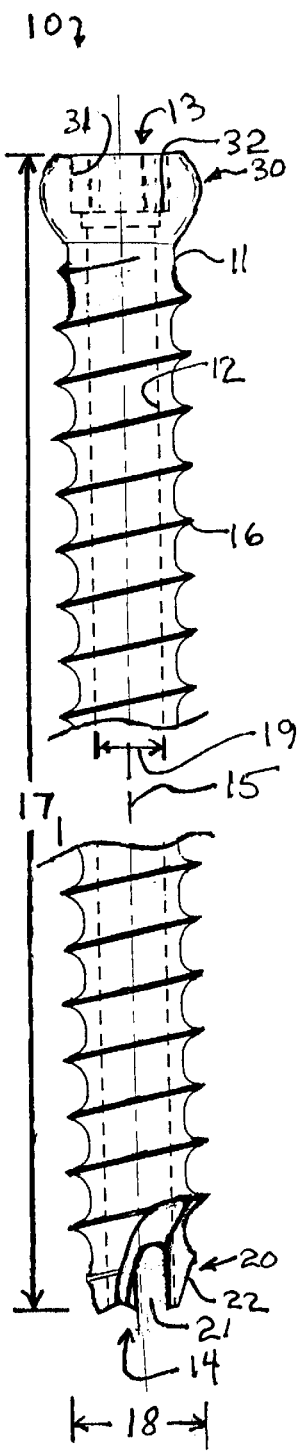
FIG. 1 is a side, plan view of a cannulated screw which can be employed in the practice of the present invention.

The invention can be further understood by the present detail, which may be read in view of the drawings. Such is to be taken in an illustrative, and not necessarily limiting, sense.

In general, the screw system of the invention is useful for transiliac fixation of at least one of a sacrum, a sacroiliac joint, and in an application in another skeletal area. It is particularly useful for repair of fractured sacra and fracture dislocations of the sacroiliac joint, which may be encountered in trauma-related presentations as well as non-emergency situations, and notably, provides for percutaneous implantation of the screw system. Quite amazingly, only two small percutaneous incisions are all that are typically required. Nonetheless, it may be employed also in standard, open surgical procedures. The system includes a cannulated bone screw that can span the iliac crests of a patient. The screw has a head, which may be engaged with a surgical tool, a shaftlike body, a tip, which may be a thread-cutting tip, and threads on at least part of the body between the first (tip) and second (head) ends, advantageously at least about the tip end; and a locknut with threads, which are generally of the bone screw type, corresponding to those of the screw for threading on the screw. Any type bone threads may be employed on the screw and locknut. For example, the threads on both the screw and the locknut can be of the cancellous type. Preferably, a washer is provided to secure the head against the appropriate surface of the bone in which the screw is implanted. The components can be made of any suitable material. Materials may include metals, plastics and ceramics. However, surgically suitable metals such as stainless steel, cobalt-chrome or titanium alloys are preferred. For example, the metal for the components can be stainless steel made to ASTM F-1314 standards.

The locknut itself can be of particular interest. It generally provides for interference fitting with the screw.

Furthermore, in general, the kit for employment in the practice of the invention can include at least one aforementioned screw system; and a guidewire, which is essentially as long as or longer than the elongate hollow body of the screw, and over which the screw can pass by way of its openings. Preferably, the guidewire is rigid and has a drill bit tip. Advantageously, a cannulated starter drill bit is provided for creating the opening in the bone prior to guidewire insertion, and through the bore of which the guidewire is inserted. Beneficially, too, a tool set to engage the head of the screw for twisting the screw so that it can thread through bone and/or engage the nut so that it can be tightened onto the first end of the screw can be provided as part of the kit. Two or more screw systems can be provided, and the tool set can include a head wrench and a nut wrench, either or both of which is/are cannulated to slide over the guidewire for efficient installation of the screw system, especially in those procedures in which percutaneous incisions are desirable. The guidewire and tool(s) can be made of any suitable material, to include stainless steel. For example, the guidewire may be made of custom-455 stainless to ASTM A-313 standards with the head and nut wrenches made of 17-4 PH stainless to ASTM A-564 standards.

With respect to the drawings, screw system 100 for repair of fractured sacra and fracture dislocations of the sacroiliac joint generally spans iliac crests 9 when implanted, and can include cannulated bone screw 10; corresponding bone-screw threaded nut 40; and washer 50. For example, the screw 10, nut 40 and washer 50 are the same grade of surgical stainless steel.

The screw 10 has elongate, hollow body 11 with inside surface 12, first opening 13 on a first end of the body 11 and second opening 14 on opposing, second end of the body 11. The screw 10 is constructed about central axis 15 which runs through the hollow body 11, and has threads 16 of the cancellous form bone screw type, say, having some ten threads to the inch (2.54 cm) with a 7.0-mm by 2.75-mm pitch. The threads are on at least part of the body between the first (tip) and second (head) ends, generally at least about the first end of the hollow body 11 but advantageously spanning substantially the distance from the first to the second ends of the hollow body 11. Dimensions and shapes of the screw 10 may vary and be any adequate for its purpose. Accordingly, length 17 may be, say, about from one to eight inches (ca. 2.5 to 20 cm), for example, about 6-¼ inches (ca. 15.5 cm). Outside and inside widths 18, 19 of the hollow body 11 including threads 16 and the inside surface 12, respectively, are beneficially defined generally by circular radii emanating from the axis 15. For example, an outside diameter 18 measured across crests of generally opposing screw threads 16 can be about 9/32 of an inch (ca. 0.75 cm) with an inside diameter 19 of about 5/32 of an inch (ca. 0.40 cm). Tip 20 is on the first end of the body 11 of the screw 10. Beneficially, the tip 20 is a thread-cutting or self-tapping type, which can engage and thread the ilia or other bone of the patient. To this end, the tip 20 may be fluted with any suitable number of flute(s) 21. Accordingly, there may be, say, three flutes 21 separating three tapping tongues 22, each with trailing relief face 23 slightly angled away from the radius, and with cutting face 24. Head 30 protrudes about the second end of the body 11 of the screw 10; it may be convex in shape, for example, bulbous and somewhat if not essentially spherical, externally. Suitable tool-engaging artifice 31 with inner tool-stopping shoulder 32 present in the head, for example, with the artifice 31 a hexagonal Allen wrench type cup, although any other suitable inner and/or outer tool-engaging artifices may be employed.

The nut 40 has suitable tool-engaging artifice 41, for example, with the artifice 41 being hexagonally faced, and may have shoulder 42 for resting on the bone 9. The nut 40 is of the locknut variety when employed on the screw 10 and has throughbore 43 in body 44, and internal threads 46 defined by a helical crest and trough arrangement corresponding to the threads 16 of the screw 10 for threading on the screw. The threads 46 are of a bone-screw type, say, having about ten threads to the inch (2.54 cm or 25.4 mm) and being generally correspondent with the threads 16 on the screw 10, for example, also being of the cancellous type. For the interference fit, screw entry internal dimension 48, say, at the trough by the shoulder-end of the throughbore 43, is slightly greater than the screw exit internal dimension 49, say again, at the trough but by the opposing end of the throughbore 43, for example, providing for an about 0.010-inch (ca. 0.25-mm) difference between troughs at the screw entry end versus the screw-exit end of the nut 40. Preferably, the threads 46 have the crests similarly tapered throughout the nut bore 43 so as to provide for an interference fit difference along with the difference provided from the trough dimensions 48, 49. This provides for the screw 10 to nut 40 major-minor, pitch-diameter locking contact, for example, direct metal-to-metal fastening and locking contact, which engenders the significantly less risk of loosening. Alternatively, either the crest or trough features themselves may provide for the interference fit.

The washer 50 has bone-resting surface 51 and head-engaging cup 52 with a concave shape in throughbore 53 corresponding with the external convex shape of the head 30. The washer 50 may be any suitable shape, for example, advantageously having C-infinity symmetry about the axis 15 and have any suitable dimensions, which can include, for example, height 57 of about 0.060 inches (ca. 1.5 mm); outer diameter 58 of about 0.500 inches (ca. 13 mm); and inner diameter 59 of about 0.281 inches (ca. 7.0 mm).

Kit 1000 includes one screw system 100 or more than one. The kit 1000 may thus have two screw systems 100, or be provided with even more screw systems 100 of various sizes so that the surgeon may choose which screw systems 100 are appropriate for implanting in a particular patient. Guidewire 60, which may be made of any suitable material, for example, surgical stainless steel, is also part of the kit 1000, and it is essentially as long as or longer than the distance 17 of the body 11 of the screw 10 of the screw system 100. For example, the guidewire 60 can be about ⅛ of an inch in diameter (ca. 0.32 cm) and some eighteen or more inches (ca. 45.7 cm plus) in length. The hollow screw 10 passes over the guidewire 60 by the screw openings 13, 14. Accordingly, the guidewire 60 can be and preferably is rigid and has drill bit tip 61 for tapping a small starter hole in the bone 9 through which the screw 10 is threaded. Preferably also, cannulated starter drill 70 with bit 71 is employed to create an initial opening in the the bone 9 which in the case of a sacral area application may be one of the two ilia. After the drill 70 has entered the iliac crest bone 9, and while it remains in place there, the guidewire 60 is inserted through the bore 72 of the drill 70 to perform its task of tapping through any remaining bone 9 of that first ilium, and, pushed through it and across to the second, opposing ilium, tapping through the bone 9 of the opposing ilium. A typical starter drill may be some six to eight inches or more (ca. 15.2 to 20.3 cm plus) in length, and have, for example, a 5-mm or so outside, drilling diameter with a 3.2-mm or so bore or cannulation through which the longer guidewire 60 may be passed. Use of the starter drill 70, which may be made of any suitable material, for instance, surgical stainless steel, is beneficial since, during a typical implant procedure, an X-ray instrument is employed, which has a limited field of view. As a consequence, the shorter starter drill 70 is more easily followed than the longer guidewire 60 would be during the incipient stages of the operation. After the starter drill 70 makes its foothold, the guidewire 60 and then the screw 10 and nut 20 follow in turn. The drill 70 is removed along the guidewire 60 when the guidewire 60 is in place before the screw 10 and nut 20 are implanted. Preferably also, additional tool set 80 is provided for engaging the head 30 of the screw 10 so as to twist the screw 10 so that it can thread through bone 9 and/or engage the nut 40 so that it can be tightened onto the first end of the screw 10. Advantageously, the tool set 80 includes cannulated tools such as T-handle Allen wrench 83 for engaging the artifices 31 of the screw head 30 and T-handle socket wrench 84 for engaging the artifices 41 of the locking nut 40. Tools of the tool set 80, including the tools 83, 84, may be made of any suitable material, for example, surgical stainless steel.

To recapitulate, in preferred practice of the invention, when embodied, for example, as a screw system 100 and/or kit 1000 adapted especially for transiliac sacral or sacroiliac joint fixation, the following particular benefits can obtain:

1. The system 100 can be installed percutaneously, when employing the guidewire 60 especially in conjunction with the drill 70 as well as when employing the additional tools 80 of the kit 1000, by requiring only two small incisions, which causes less surgical trauma to the patient than with other methods, systems and kits.
2. The system 100, being cannulated, when installed, the guidewire drill 60 acts as a targeting device to accurately guide the self-tapping bone screw 10 over the fracture or dislocation site.
3. Fixation of the fracture or dislocation site with the system 100 can provide for maximum compression.
4. The metal-to-metal interference fit between the screw 10 and locknut 40 provides for a better, more secure fixation than with other screw and nut systems in particular, and any possibility for release or backoff which causes loosening is substantially reduced if not eliminated.

Similar if not the same benefits apply when the invention is applied to other skeletal areas of the body, whether human or vertebrate animal. Application of the invention to human patients is beneficially practiced.

The components of the screw system 100 and kit 1000 can be made in any suitable manner. For example, casting or forging with later machining may be employed. As such, one of skill in this art would recognize how to make the invention.

The system 100 is to be implanted through orthopedic surgery, particularly trauma. The kit 1000 assists greatly in the implantation. As such, one of skill in that art would recognize how to use the invention.

CONCLUSION

The present invention is thus provided. Various features, parts, subcombinations and combinations may be employed with or without reference to other features, parts, subcombinations or combinations in the practice of the invention, and numerous and sundry adaptations and modifications can be effected within its spirit, the literal claim scope of which is particularly pointed out as follows:

We claim:

1. A screw system useful for transiliac fixation of at least one of a sacrum and a sacroiliac joint, or in a fixation application to another skeletal area, comprising:
    a cannulated bone screw having an elongate, hollow body with openings on a first end of the body and on an opposing, second end of the body; a tip on the first end of the body; a head about the second end of the body, which can be engaged with a surgical tool; and threads on at least part of the body between the first and second ends; and a locknut with threads generally corresponding to those of the screw for threading on the screw wherein the locknut can lock itself on the screw through an interference fitting with the screw.

2. The system of claim 1, which is useful for the transiliac fixation of at least one of a sacrum and a sacroiliac joint, with the screw of a length sufficient to span iliac crests of a patient, and the tip being capable of engaging and threading ilia of the patient, and the locknut providing for a major-minor, pitch diameter interference fit with the screw.

3. The system of claim 2, wherein the tip is thread-cutting.

4. The system of claim 3, having cancellous form threads.

5. A screw system useful for transiliac fixation of at least one of a sacrum and a sacroiliac joint, or in a fixation application to another skeletal area, comprising:
  a cannulated bone screw having an elongate, hollow body with openings on a first end of the body and on an opposing, second end of the body; a tip on the first end of the body; a head about the second end of the body, which can be engaged with a surgical tool; and threads on at least part of the body between the first and second ends;
  a locknut with threads generally corresponding to those of the screw for threading on the screw beginning by being placed over the first end of the body of the screw; and
  a washer.

6. The system of claim 5, which is useful for the transiliac fixation of at least one of a sacrum and a sacroiliac joint, with the screw of a length sufficient to span iliac crests of a patient, the tip being capable of engaging and threading ilia of the patient, and the locknut providing for a major-minor, pitch diameter interference fit with the screw.

7. The system of claim 6, wherein the tip is thread-cutting.

8. The system of claim 7, having cancellous form threads.

9. A screw system useful for transiliac fixation of at least one of a sacrum and a sacroiliac joint, or in a fixation application to another skeletal area, comprising:
  a cannulated bone screw having an elongate, hollow body with openings on a first end of the body and on an opposing, second end of the body; a tip on the first end of the body; a head about the second end of the body, which can be engaged with a surgical tool; and threads on at least part of the body between the first and second ends;
  a locknut with threads generally corresponding to those of the screw for threading on the screw; and
  a washer
  wherein the head has an external convex shape, and the washer has a throughbore with a shoulder and an adjacent surface in the throughbore having a concave shape corresponding with the external shape of the head.

10. The system of claim 9, which has cancellous form threads and is useful for the transiliac fixation of at least one of a sacrum and a sacroiliac joint, with the screw having a length sufficient to span iliac crests of a patient, the tip being thread-cutting and capable of engaging and threading the ilia of the patient, and the locknut providing for a major-minor, pitch diameter interference fit with the screw.

11. A locknut comprising a body having a threaded bore with threads of a bone screw type, wherein an interference locking taper is provided to at least one of trough and crest features of the threads so that locking of at least one of the trough and crest features of the locknut can be carried out with respect to at least one of crest and trough features of threads of a threaded screw on which the locknut can be correspondingly threaded.

12. The locknut of claim 11, wherein the threads of the locknut are of a cancellous form and can provide for major-minor, pitch-diameter interference fit with the screw.

13. A kit useful for transiliac fixation of at least one of a sacrum and a sacroiliac joint, or in an application to another skeletal area, comprising at least one screw system including a cannulated bone screw having an elongate, hollow body with openings on a first end of the body and on an opposing, second end of the body; a tip on the first end of the body; a head about the second end of the body, which can be engaged with a surgical tool; and threads on at least part of the body between the first and second ends; and a locknut with threads generally corresponding to those of the screw for threading on the screw; and a guidewire, which is rigid and has a drill bit tip and is essentially as long as or longer than the elongate hollow body of the screw of the at least one screw system, and over which the screw can pass by the openings in the hollow body of the screw.

14. The kit of claim 13, which also contains a tool set to engage the head of the screw for twisting the screw so that it can do at least one of the following: thread through bone, and engage the nut so that it can be tightened onto the first end of the screw.

15. The kit of claim 14, wherein a cannulated starter drill is also present.

16. The kit of claim 15, wherein a washer is also present.

17. The kit of claim 14, wherein a washer is also present.

18. The kit of claim 13, wherein a washer is also present.

19. A kit useful for transiliac fixation of at least one of a sacrum and a sacroiliac joint, or in an application to another skeletal area, comprising:
  at least one screw system including
    a cannulated bone screw having an elongate, hollow body with openings on a first end of the body and on an opposing, second end of the body; a tip on the first end of the body; a head about the second end of the body, which can be engaged with a surgical tool; and threads on at least part of the body between the first and second ends; and
    a locknut with threads generally corresponding to those of the screw for threading on the screw, wherein the locknut can lock itself on the screw through an interference fitting with the screw;
  and a guidewire, which is essentially as long as or longer than the elongate hollow body of the screw of the at least one screw system, and over which the screw can pass by the openings in the hollow body of the screw.

20. The kit of claim 19, wherein the screw has a length sufficient to span iliac crests of a patient, and the tip can engage and thread ilia of the patient; the interference fitting is a major-minor, pitch-diameter interference fit between the screw and locknut; and a cannulated starter drill and a washer are also present.

21. A screw system useful for transiliac fixation of at least one of a sacrum and a sacroiliac joint, or in a fixation application to another skeletal area, comprising:
  a cannulated bone screw having an elongate, hollow body with openings on a first end of the body and on an opposing, second end of the body; a tip on the first end of the body; a head about the second end of the body, which can be engaged with a surgical tool; and threads having crest and trough features on at least part of the body between the first and second ends; and
  a locknut including a body having a threaded bore with threads of a bone screw type, wherein an interference locking taper is provided to at least one of trough and crest features of the threads of the locknut, with the threads of the locknut generally corresponding to those of the screw for threading on the screw wherein locking of at least one of the trough and crest features of the locknut can be carried out with respect to at least one of the crest and trough features of the threads of a threaded screw on which the locknut can be threaded.

22. The system of claim 21, wherein the threads of the screw are of a cancellous form.

23. A screw system useful for transiliac fixation of at least one of a sacrum and a sacroiliac joint, or in a fixation application to another skeletal area, comprising:

a cannulated bone screw having an elongate, hollow body with openings on a first end of the body and on an opposing, second end of the body; a tip on the first end of the body; a head about the second end of the body, which can be engaged with a surgical tool; and threads on at least part of the body between the first and second ends; and a single nut, which functions as a one-piece locknut subsystem, and which nut has threads generally corresponding to those of the screw for threading on the screw.

24. The system of claim 23, wherein the locknut subsystem provides for a major-minor, pitch diameter interference fit with the screw.

25. A screw system useful for transiliac fixation of at least one of a sacrum and a sacroiliac joint, or in an application to another skeletal area, comprising:

a cannulated bone screw having an elongate, hollow body with openings on a first end of the body and on an opposing, second end of the body; a tip on the first end of the body; a head essentially at the second end of the body, which can be engaged with a surgical tool for installing the screw; and threads on at least part of the body between the first and second ends; and a locknut with threads generally corresponding to those of the screw for threading on the screw beginning by being placed over the first end of the body of the screw.

26. The system of claim 25, wherein the screw has a length from the first end to the second end of the body from about 6-¼ inches to about 8 inches.

27. The system of claim 26, wherein a washer is present.

* * * * *

UNITED STATES PATENT AND TRADEMARK OFFICE
CERTIFICATE OF CORRECTION

PATENT NO. : 6,635,059 B2  
DATED : October 21, 2003  
INVENTOR(S) : Randall et al.

Page 1 of 3

It is certified that error appears in the above-identified patent and that said Letters Patent is hereby corrected as shown below:

Drawings,
Replace FIGS. 1-11 with formal FIGS. 1-11, as follows:

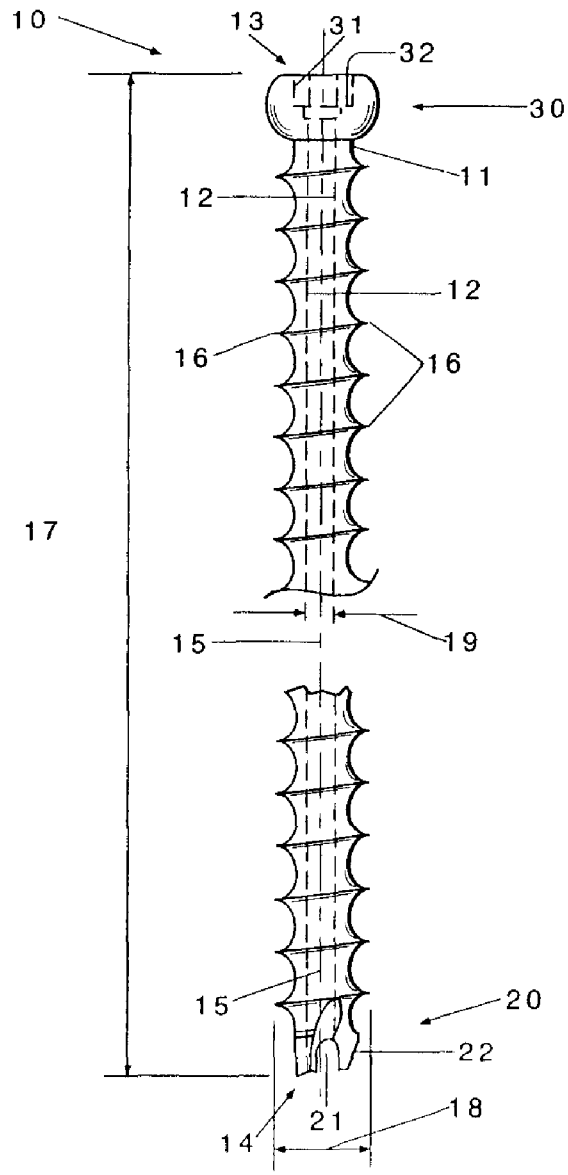

Fig. 1

UNITED STATES PATENT AND TRADEMARK OFFICE
CERTIFICATE OF CORRECTION

PATENT NO. : 6,635,059 B2  Page 2 of 3
DATED : October 21, 2003
INVENTOR(S) : Randall et al.

Figure 2:
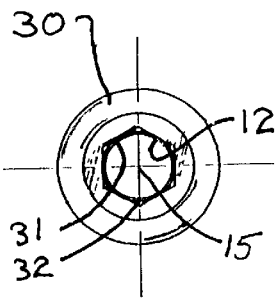
FIG. 2 is a top view of the cannulated screw of FIG. 1, particularly depicting its head.

It is certified that error appears in the above-identified patent and that said Letters Patent is hereby corrected as shown below:

Drawings (cont'd),

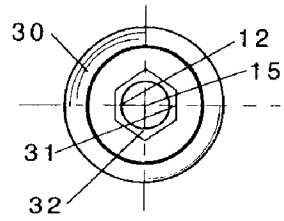
Fig. 2

Figure 5:
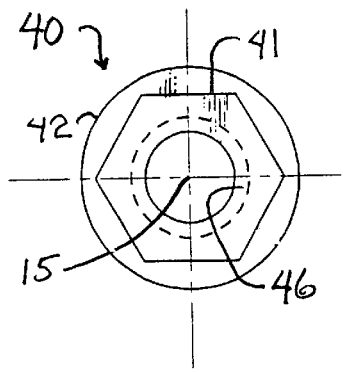
FIG. 5 is a bottom, plan view of a locking nut for the cannulated screw of FIG. 1, which can be employed in the practice of the present invention.

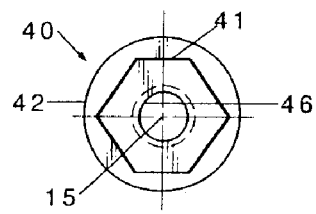
Fig. 5

Figure 3:
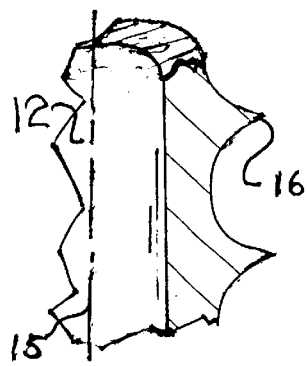
FIG. 3 is a side sectional view of part of the cannulated screw of FIG. 1, particularly depicting its threads.

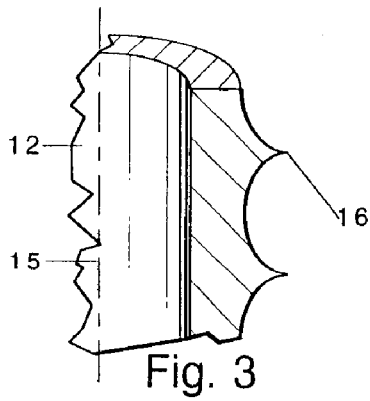
Fig. 3

Figure 6:
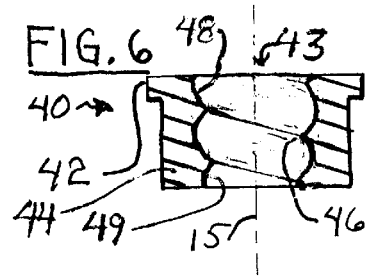
FIG. 6 is a side, sectional view of the nut of FIG. 5.

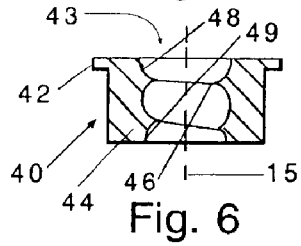
Fig. 6

Figure 7:
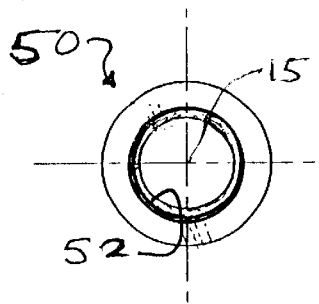
FIG. 7 is a top view of a washer for the head of the cannulated screw of FIG. 1, which can be employed in the practice of the present invention.

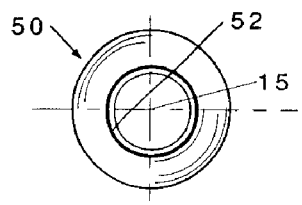
Fig. 7

Figure 4:
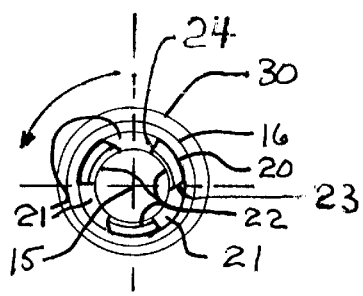
FIG. 4 is a bottom view of the cannulated screw of FIG. 1, particularly depicting its self-threading tip.

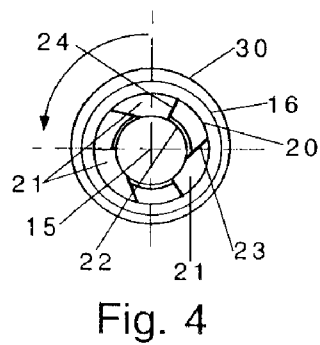
Fig. 4

Figure 8:
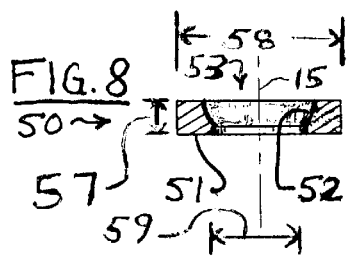
FIG. 8 is a side, sectional view of the washer of FIG. 7.

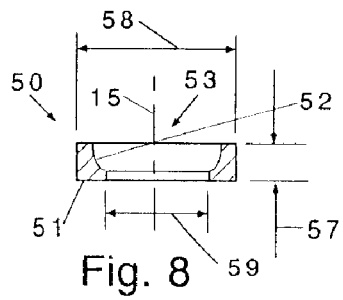
Fig. 8

UNITED STATES PATENT AND TRADEMARK OFFICE
CERTIFICATE OF CORRECTION

PATENT NO.   : 6,635,059 B2                                   Page 3 of 3
DATED        : October 21, 2003
INVENTOR(S)  : Randall et al.

It is certified that error appears in the above-identified patent and that said Letters Patent is hereby corrected as shown below:

Drawings, (cont'd)

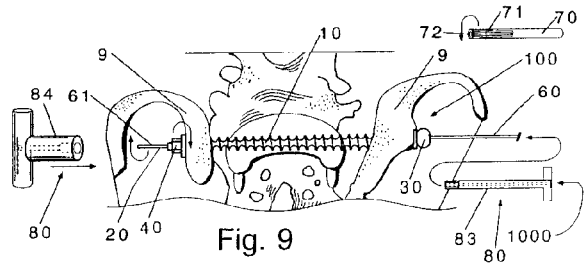

Fig. 9

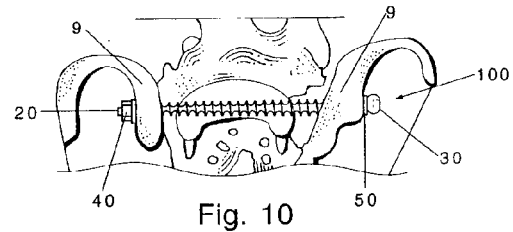

Fig. 10

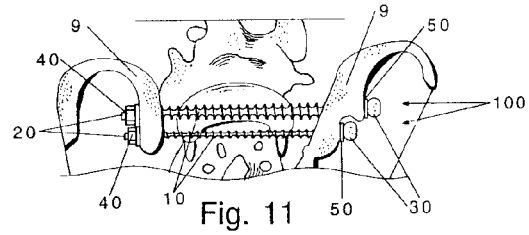

Fig. 11

Signed and Sealed this

Seventeenth Day of February, 2004

JON W. DUDAS
*Acting Director of the United States Patent and Trademark Office*